(12) United States Patent
Juuti et al.

(10) Patent No.: US 9,551,659 B2
(45) Date of Patent: Jan. 24, 2017

(54) OPTICAL APPARATUS AND METHOD FOR FLUORESCENCE MEASUREMENT OF ANALYTES COMPRISING BACKSCATTERING DETECTION

(71) Applicant: TEKNOLOGIAN TUTKIMUSKESKUS VTT, VTT (FI)

(72) Inventors: Mikko Juuti, Kuopio (FI); Pekka Teppola, Varkaus (FI)

(73) Assignee: TEKNOLOGIAN TUTKIMUSKESKUS VTT, VTT (FI)

(\*) Notice: Subject to any disclaimer, the term of this patent is extended or adjusted under 35 U.S.C. 154(b) by 183 days.

(21) Appl. No.: 14/351,067

(22) PCT Filed: Oct. 10, 2012

(86) PCT No.: PCT/FI2012/050973
§ 371 (c)(1),
(2) Date: Apr. 10, 2014

(87) PCT Pub. No.: WO2013/053998
PCT Pub. Date: Apr. 18, 2013

(65) Prior Publication Data
US 2014/0234984 A1    Aug. 21, 2014

(30) Foreign Application Priority Data

Oct. 11, 2011    (FI) ................................. 20115999

(51) Int. Cl.
*G01N 21/76* (2006.01)
*G01N 21/00* (2006.01)
(Continued)

(52) U.S. Cl.
CPC .............. *G01N 21/64* (2013.01); *G01N 21/33* (2013.01); *G01N 21/532* (2013.01);
(Continued)

(58) Field of Classification Search
CPC ... A61B 5/0075; A61B 5/0071; A61B 5/0059; A61B 1/043; A61B 1/00186; A61B 5/0066; A61B 5/0068; A61B 1/07; A61B 5/1079; A61B 1/00172; A61B 1/0638; A61B 5/0062; A61B 1/00096; A61B 1/00165
See application file for complete search history.

(56) References Cited

U.S. PATENT DOCUMENTS 4,192,996 A * 3/1980 Kronick ................. G01N 21/33
250/373
4,500,641 A    2/1985 van den Engh et al.
(Continued)

FOREIGN PATENT DOCUMENTS

JP    11-258512 A    9/1999
JP    2011-179904 A    9/2011

OTHER PUBLICATIONS

Finnish Search Report issued in Finnish Application No. 20115999 on Jan. 3, 2012.
(Continued)

*Primary Examiner* — Yelena G Gakh
(74) *Attorney, Agent, or Firm* — Birch, Stewart, Kolasch & Birch, LLP

(57) ABSTRACT

An optical apparatus comprises an ultraviolet light source (100) configured to transmit the ultraviolet light to a sample (102), one or more wavelength dependent beam splitters (104) and at least two separate detectors (106, 108). Each beam splitter (104) receives, from the sample (102), a band of excitating ultraviolet light and at least one band of fluorescence associated with an interaction between the excitating ultraviolet light and the sample (102) in the optical path through the sample (102), directs the band of excitating ultraviolet light passed through the sample (102) towards a first detector (106), and directs the at least one
(Continued)

band of the fluorescence towards at least one separate detector (108). The first detector (106) and the at least one separate detector (108) are simultaneously configured to form electrical signals carrying information on powers of the bands of the ultraviolet light and the fluorescence, respectively. The signal processing unit (110) configured to measure the at least one property of the sample (102) on the basis of a signal from the first detector (106) and each signal from the at least one separate detector (108).

18 Claims, 5 Drawing Sheets

(51) Int. Cl.
    *G01N 21/64*     (2006.01)
    *G01N 21/33*     (2006.01)
    *G01N 21/53*     (2006.01)
    *G02B 27/14*     (2006.01)
    *G01N 21/47*     (2006.01)
    *G01N 21/17*     (2006.01)

(52) U.S. Cl.
    CPC ............... *G01N 2021/1734* (2013.01); *G01N 2021/4709* (2013.01); *G01N 2021/6439* (2013.01); *G02B 27/141* (2013.01)

(56) References Cited

U.S. PATENT DOCUMENTS

| | | | | |
|---|---|---|---|---|
| 4,994,671 | A | * | 2/1991 | Safinya ................. E21B 47/102 |
| | | | | 250/253 |
| 5,252,834 | A | * | 10/1993 | Lin ..................... G01N 21/6408 |
| | | | | 250/458.1 |
| 5,329,352 | A | * | 7/1994 | Jacobsen ................... G01J 3/02 |
| | | | | 356/301 |
| 5,489,977 | A | | 2/1996 | Winslow et al. |
| 5,698,397 | A | | 12/1997 | Zarling et al. |
| 5,946,431 | A | | 8/1999 | Fernandes |
| 2001/0007496 | A1 | | 7/2001 | Modlin et al. |
| 2001/0012151 | A1 | * | 8/2001 | Knebel ............... G02B 21/0076 |
| | | | | 359/368 |
| 2003/0058450 | A1 | | 3/2003 | Mosley et al. |
| 2004/0178044 | A1 | | 9/2004 | Mori et al. |
| 2006/0188869 | A1 | | 8/2006 | Zeskind et al. |
| 2011/0068007 | A1 | | 3/2011 | Pang et al. |

OTHER PUBLICATIONS

Suzuki, Y. et al., "Development of a Simple and Low-cost Device for Fluorometric Determination of Selenium in Water Samples", Analytical Sciences, 2010, vol. 26, pp. 719-722, Kofu, Japan.
Supplementary European Search Report issued in European Application No. 12 84 0026 on Oct. 8, 2014.

\* cited by examiner

OPTICAL APPARATUS AND METHOD FOR FLUORESCENCE MEASUREMENT OF ANALYTES COMPRISING BACKSCATTERING DETECTION

FIELD

The invention relates to an optical measurement and particularly to a measurement based on fluorescence.

BACKGROUND

When a fluorescent compound absorbs ultraviolet light, for example, it may emit light in an optical band having longer wavelength than the ultraviolet light. The optical band of emission may take place as visible light, for instance.

Fluorescence may be applied in a plurality of fields such as measurements of chemical and/or biological fluid samples, for example. The samples may have natural fluorescence or fluorescent reagents may be added to the sample. A chemical and/or biological process may change the amount of fluorescent reagent or compound in the sample and hence by measuring the strength of fluorescence it is possible to determine the progress or quality of the process.

Fluorescence is usually measured by directing ultraviolet light to a sample and by receiving forward scattered fluorescent optical radiation typically in the visible band by a detector. The detector, which may comprise a dispersing element and photomultipliers in front of each detecting element, transforms the received spectrum of optical radiation into an electrical signal which may further be converted into a digital form. The digital spectrum may be analyzed and the concentration of the fluorescent compound in the sample determined by a computer with a suitable signal processing program.

However, both the measurement arrangement and the optical and electrical signal processing are complicated. Moreover, low cost detectors for measuring ultraviolet absorption and ultraviolet fluorescence are not available at the moment. Additionally, calibration of the fluorescence measurement is difficult which deteriorates the accuracy of the measurement. Hence, there is a need for a low cost and accurate device for measuring fluorescence.

SUMMARY

The following presents a simplified summary of the invention in order to provide a basic understanding of some aspects of the invention. Its purpose is to present some concepts of the invention in a simplified form as a prelude to the more detailed description that is presented later.

An aspect of the invention relates to an optical apparatus, characterized in that the apparatus comprises an ultraviolet light source configured to transmit the ultraviolet light to a sample, one or more wavelength dependent beam splitters, at least one backscattering beam splitter, at least two back scattering detectors, and at least two separate detectors, wherein:

each beam splitter is configured to receive, from the sample, a band of excitating ultraviolet light and at least one band of fluorescence associated with an interaction between the excitating ultraviolet light and the sample in the optical path through the sample, to direct the band of excitating ultraviolet light passed through the sample towards a first detector, and to direct the at least one band of the fluorescence towards at least one separate detector;

the first detector and the at least one separate detector are simultaneously configured to form electrical signals carrying information on powers of the bands of the ultraviolet light and the fluorescence, respectively;

the at least one backscattering beam splitter is configured to receive ultraviolet light and fluorescence scattered backwards from the sample from a direction different from parallel to the transmitted ultraviolet light, and direct them to different back scattering detectors;

the at least two back scattering detectors are configured to separately detect ultraviolet light and fluorescence scattered backwards from the sample; and a signal processing unit is configured to measure the at least one property of the sample on the basis of a signal from the first detector and each signal from the at least one separate detector, and to calibrate the measurement of the at least one property on the basis of the back scattering for compensating additional scattering in the optical path or in the sample.

An aspect of the invention relates to an optical method, characterized by: transmitting by an ultraviolet light source ultraviolet light to a sample; detecting, by at least two back scattering detectors, ultraviolet optical radiation and fluorescence scattered backwards from the sample from a direction different from parallel to the transmitted ultraviolet light;

receiving, from the sample, a band of excitating ultraviolet light and at least one band of fluorescence associated with an interaction between the excitating ultraviolet light and the sample in the optical path through the sample, directing the band of excitating ultraviolet light passed through the sample towards a first detector, and directing the at least one band of the fluorescence towards at least one separate detector by a beamsplitter;

forming simultaneously, by the first detector and at least one separate detector, electrical signals carrying information on powers of the of the bands of the ultraviolet light and the fluorescence, respectively;

measuring, by a signal processing unit, at least one property of the sample on the basis of an optical power of the ultraviolet light and an optical power of the fluorescence in at least one separate detector; and calibrating, by the signal processing unit, the measurement of the at least one property on the basis of the back scattering for compensating additional scattering in the optical path or in the sample.

A still further aspect of the invention relates to an apparatus comprising: at least one processor; and at least one memory including a computer program code, wherein the at least one memory and the computer program code are configured, with the at least one processor, to cause the apparatus to:

detect, by at least two back scattering detectors ultraviolet optical radiation and fluorescence scattered backwards from the sample from a direction different from parallel to the transmitted ultraviolet light;

transmit, by an ultraviolet light source, ultraviolet light to a sample; form simultaneously, by a first detector and at least one separate detector, electrical signals carrying information on powers of the of the bands of the ultraviolet light and the fluorescence, respectively, on the basis of splitting, by a beamsplitter, of a band of excitating ultraviolet light and at least one band of fluorescence associated with an interaction between the excitating ultraviolet light and the sample in the optical path through the sample towards the first detector, and the at least one separate detector;

measure, in a signal processing unit, at least one property of the sample on the basis of an optical power of the ultraviolet light and an optical power of the fluorescence in at least one separate detector; and calibrate, by the signal processing unit, the measurement of the at least one property on the basis of the back scattering for compensating additional scattering in the optical path or in the sample.

Although the various aspects, embodiments and features of the invention are recited independently, it should be appreciated that all combinations of the various aspects, embodiments and features of the invention are possible and within the scope of the present invention as claimed.

The present solution provides advantages. The apparatus and method of the measurement is simple. Low cost detectors for measuring ultraviolet absorption and ultraviolet fluorescence may be used. Additionally, calibration of the fluorescence measurement may easily be performed.

BRIEF DESCRIPTION OF THE DRAWINGS

In the following the invention will be described in greater detail by means of exemplary embodiments with reference to the attached drawings, in which.

DESCRIPTION OF EMBODIMENTS

Exemplary embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
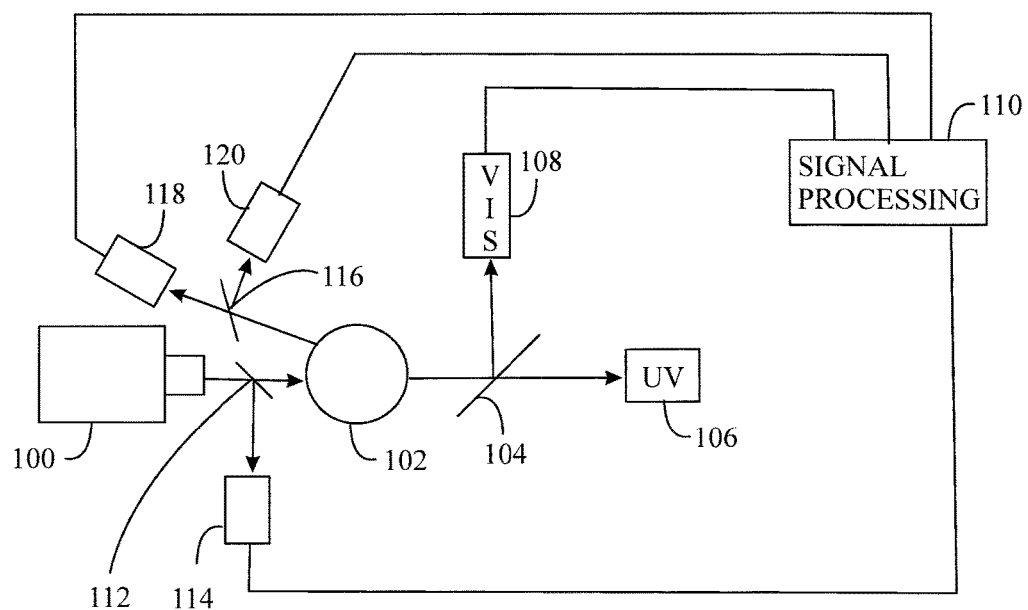
FIG. 1 shows a basic configuration of the measuring arrangement.

FIG. 1 presents an apparatus for the optical measurement. The apparatus comprises an ultraviolet light source 100 for transmitting ultraviolet light to a sample 102, a wavelength dependent beam splitter 104, two separate detectors 106, 108. Additionally, a signal processing unit 110 may be included. The ultraviolet light source 100 may comprise a led (light emitting diode) or a laser. Alternatively or additionally, the ultraviolet light source 100 may comprise a fluorescent lamp, gas-discharge lamp or the like. Moreover, the ultraviolet light source 100 may comprise for example at least one optical filter which may be a narrow band filter such as a notch filter or a wide band filter such as a high pass filter. Ultraviolet light is electromagnetic radiation including wavelengths about 10 nm to 400 nm in an optical range. The optical radiation, in turn, may range about 10 nm to 500 nm.

The beam splitter 104 may in principle be a dichroic mirror or a dichroic prism that split a beam of light into two or more beams. The beam splitter 104 may pass optical radiation whose wavelength is longer than a threshold wavelength and reflect the rest of the optical radiation used in the measurement. Alternatively, the beam splitter 104 may pass optical radiation whose wavelength is shorter than a threshold wavelength and reflect the rest of the optical radiation. The threshold wavelength may be between the ultraviolet light and visible light. The threshold wavelength may be 400 nm, for example.

The beam splitter 104 receives, from the sample 102, a band of excitating ultraviolet light transmitted by the ultraviolet light source 100. The beam splitter 104 also receives at least one band of fluorescence associated with an interaction between the excitating ultraviolet light and the sample 102 in the optical path through the sample 102 if the sample 102 has fluorescent substance. Usually, fluorescence is observed in longer wavelengths than the excitation radiation. Hence, fluorescence may be detected in a band of visible light.

In this example, the beam splitter 104 directs the band of excitating ultraviolet light passed through the sample 102 towards a first detector 106, and the beam splitter 104 directs the visible light of fluorescence towards the separate detector 108. In FIG. 1, the beam splitter 104 passes the band of excitating ultraviolet light through itself to the detector 106 and reflects the visible light generated in the fluorescence interaction to the detector 108.

The first detector 106 transforms the received ultraviolet light into an electric signal which carries information on the power of the ultraviolet light.

Similarly, the separate detector 108 forms an electrical signal carrying information on the power of the fluorescence. Both the first detector 106 and the separate detector 108 may form the powers simultaneously.

In an embodiment, the signal processing unit 110 receives the analog or digital signals from the detectors 106, 108 and measures the at least one property of the sample on the basis of an optical power of the ultraviolet light and an optical power of the fluorescence. One of the detectors 106, 108 is used to measure power of fluorescence and another of the detectors 106, 108 is used to measure absorption of the ultraviolet light. The signals carrying information on powers of the ultraviolet light and the fluorescence are also received simultaneously in the signal processing unit 110. An analog signal may be converted into a digital form in the signal processing unit 110 before processing.

The signal processing unit 110 may comprise a processor, memory and a suitable computer program for processing the signals.

Additionally, the apparatus may comprise a partially transparent reflector 112 and a reference detector 114. The partially transparent reflector 112 is placed between the ultraviolet light source 100 and the sample 102. The partially transparent reflector 112, which acts as a beam slitter, may reflect a known part of the ultraviolet light transmitted by the ultraviolet light source 100 to the reference detector 114 which feeds an electrical signal, which carries information on the power, to the signal processing unit 110. The transparent reflector 112 may be a piece of glass, for example, reflecting a few percent of the received optical radiation to the reference detector 114. The signal processing unit 110 measures the transmission power of the ultraviolet light source 100 on the basis of the electrical signal. The signal processing unit 110 may scale the powers of the ultraviolet light passed through the sample 102 and the fluorescence by dividing them by the measured power. Hence, even if the optical power of the ultraviolet light source 100 varies, the relative part passed through the sample and the relative part of the power shifted to lower wavelengths may be determined.

The signal processing unit 110 may also determine the attenuation of the sample 102 in the ultraviolet light. The attenuation depends on the attenuation coefficient of the sample 102 and the length of the optical path through the sample 102. The length of the optical path and the thickness of the sample 102 which basically mean the same may be from a millimeter to tens of centimeters, for example. The attenuation coefficient, in turn, depends on an absorption coefficient and a scattering coefficient. The scattering coefficient depends on the number and the size of the scattering particles. The number of the particles depends on the consistency of the sample 102.

The ratio of the power of the fluorescence and the power of the ultraviolet light received at the detector 106 may represent a percentage of the fluorescent substance in the sample which may change in the process due to chemical reactions.

Moreover, the apparatus may comprise means for measuring back scattering which resembles the means 104, 106, 108 for measuring ultraviolet light and the fluorescence behind the sample 102. The apparatus may comprise a wavelength dependent beam splitter 116 similar to beam splitter 104, two back scattering detectors 118, 120. The detector 118 may receive ultraviolet light scattered back and the detector 120 may receive back scattered fluorescence in the range of visible light. The back scattering detectors 118, 120 feed electrical signals carrying information on the power of the received optical signals to the signal processing unit 110 which may calibrate the measurement of the at least one property on the basis of the power of the back scattering. The purpose of measuring the back scattering is to control and compensate for any additional physical scattering due to particles in the optical part of the apparatus. The measurement of back scattering enhances stability of the apparatus. The calibration measurement is used to compensate for the additional scattering such as muddiness, cloudiness or turbidity in the optical path or in the sample.

Figure 2:
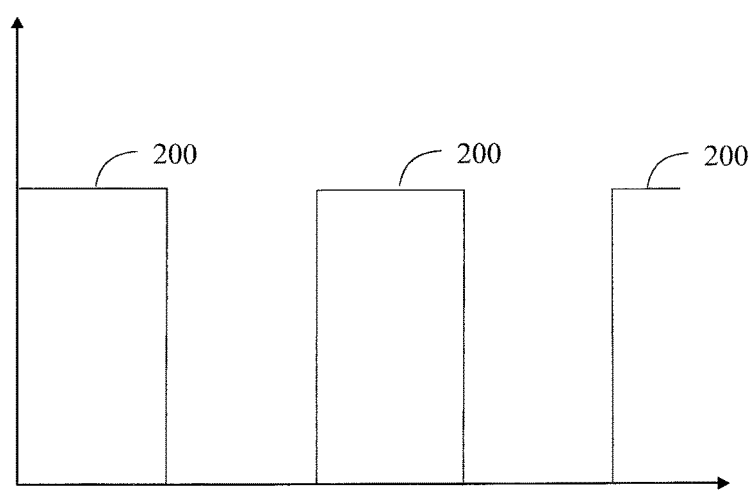
FIG. 2 shows pulses of optical radiation.

FIG. 2 shows pulses of light. The ultraviolet light source 100 may transmit ultraviolet light pulses 200 periodically. The pulses of ultraviolet light may be formed by pulsing electrically the ultraviolet light source 100 or by using a separate chopper for chopping the beam of ultraviolet light. The use of pulsed ultraviolet light enables an efficient ambient and stray light compensation with phase sensitive detection. Often, the optical power of the ultraviolet light pulses 200 varies. If, however, the power of each of the pulses is measured using the transparent reflector 112 and the reference detector 114, the relative part passed through the sample 102 and/or the relative part of the power shifted to lower wavelengths may be determined.

There is a plurality of variations in the configuration of the apparatus. In general, the apparatus comprises an ultraviolet light source 100 configured to transmit the ultraviolet light to a sample 102, one or more wavelength dependent beam splitters 104 and at least two separate detectors 106, 108. The beam splitter 104 may be a trichroic prism or the like instead of being dichroic. In general, the apparatus may comprise more than two back scattering detectors.

Figure 3:
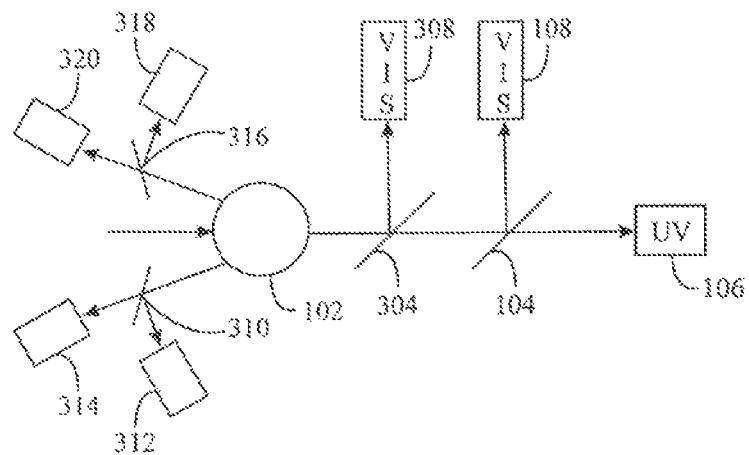
FIG. 3 shows the apparatus with two backscattering detectors.

FIG. 3 shows the apparatus with four backscattering detectors 312, 314, 318, 320 and two backscattering beam splitters 310, 316. In general, the optical radiation backscattering out of the sample 102 may be measured at a narrow (plane) angle or even at a wide solid angle, whose value may go up to almost $4\pi$, around the sample 102. In the example of FIG. 3, the first backscattering beam splitter 310 may have a threshold wavelength at 400 nm, for instance, such that the wavelengths longer than 400 nm will reflect to the detector 312 but the wavelength at or shorter than 400 nm (i.e. ultraviolet) will pass through the beam splitter 310 to the detector 314. The second backscattering beam splitter 316 may also pass the wavelengths shorter than 400 nm including the ultraviolet light to the detector 320 and reflect the wavelengths at or longer than 400 nm to the detector 318.

The fluorescence may also be detected at two different visible bands using two beam splitters 104, 304 and two detectors 108, 308, for instance. The first beam splitter 304 may have a threshold wavelength at 500 nm, for instance, such that the wavelengths longer than 500 nm will reflect to the detector 308 but the wavelength at or shorter than 500 nm will pass through the beam splitter 304. The second beam splitter 104 may pass the wavelengths shorter than 400 nm including the ultraviolet light transmitted by the ultraviolet light source 100 to the detector 106 and reflect the wavelengths at or longer than 400 nm to the detector 108. That is, the second beam splitter 104 reflects the band 400 nm to 500 nm to the detector 108.

Figure 4:
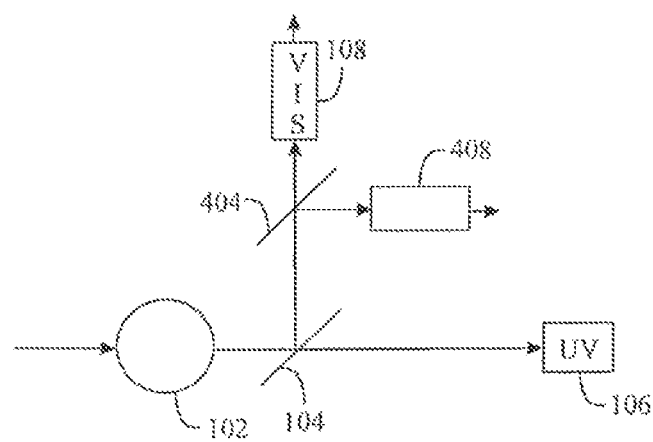
FIG. 4 shows a different configuration for visible light.

FIG. 4 shows a different configuration for visible light. The beam splitter 104 may reflect visible light to a secondary beam splitter 404 which may further divide the band of received visible light into two. A desired wavelength band of the visible light may pass through the secondary beam splitter 404 to a detector 108 and the rest of the visible light may be reflected to a detector 408. The threshold wavelength, at which the reflection stops and transmission starts, may freely be selected. The band of light reflecting from the beam splitter 404 may have shorter wavelengths than the band of light passing through the beam splitter or vice versa.

Figure 5:
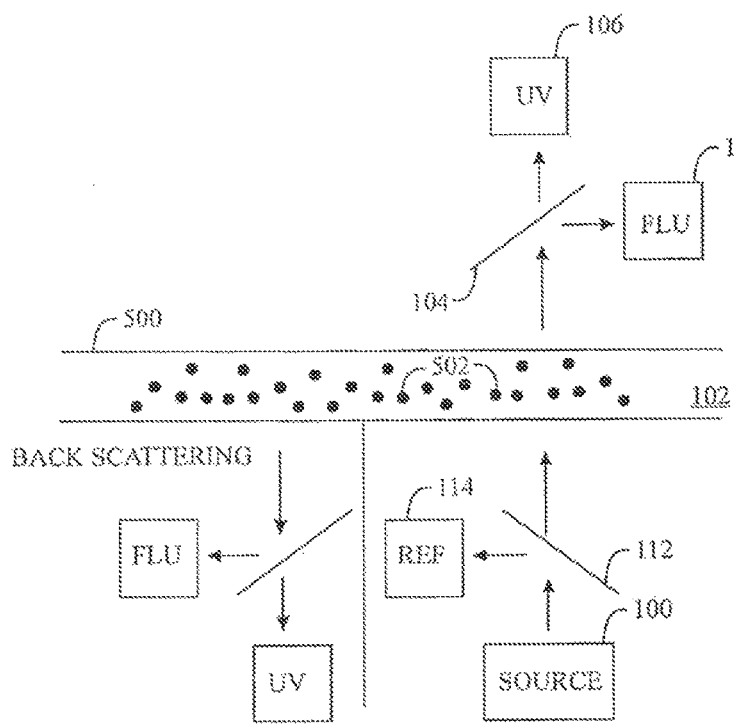
FIG. 5 shows an online analyzer.
Figure 6:
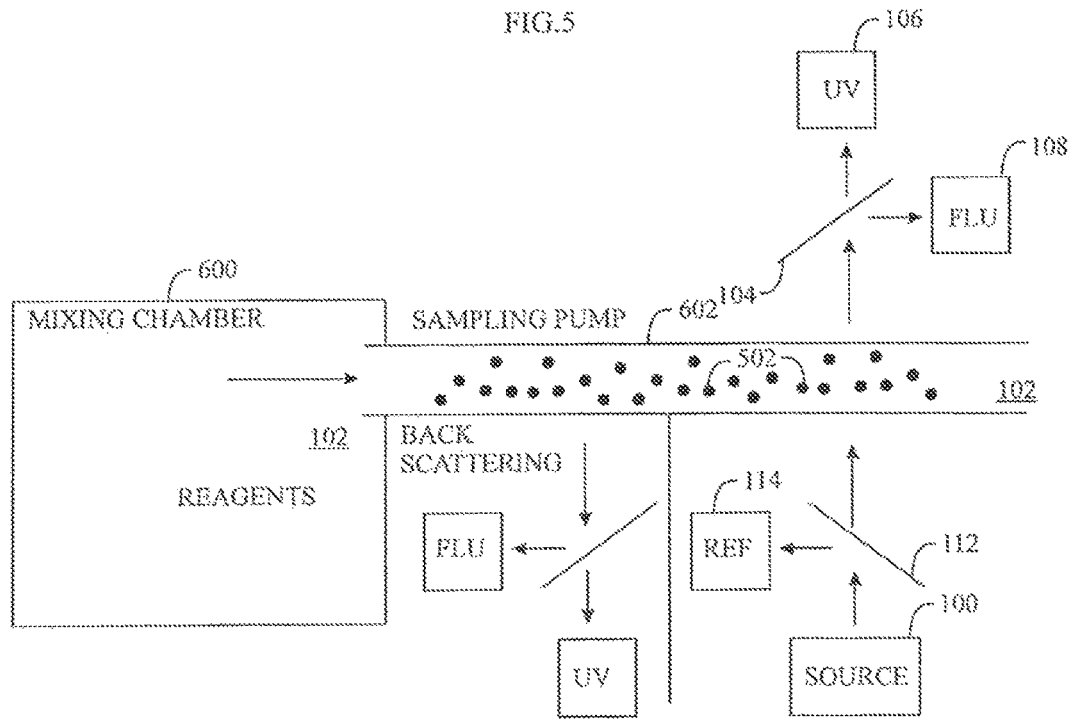
FIG. 6 shows a portable kit.
Figure 7:
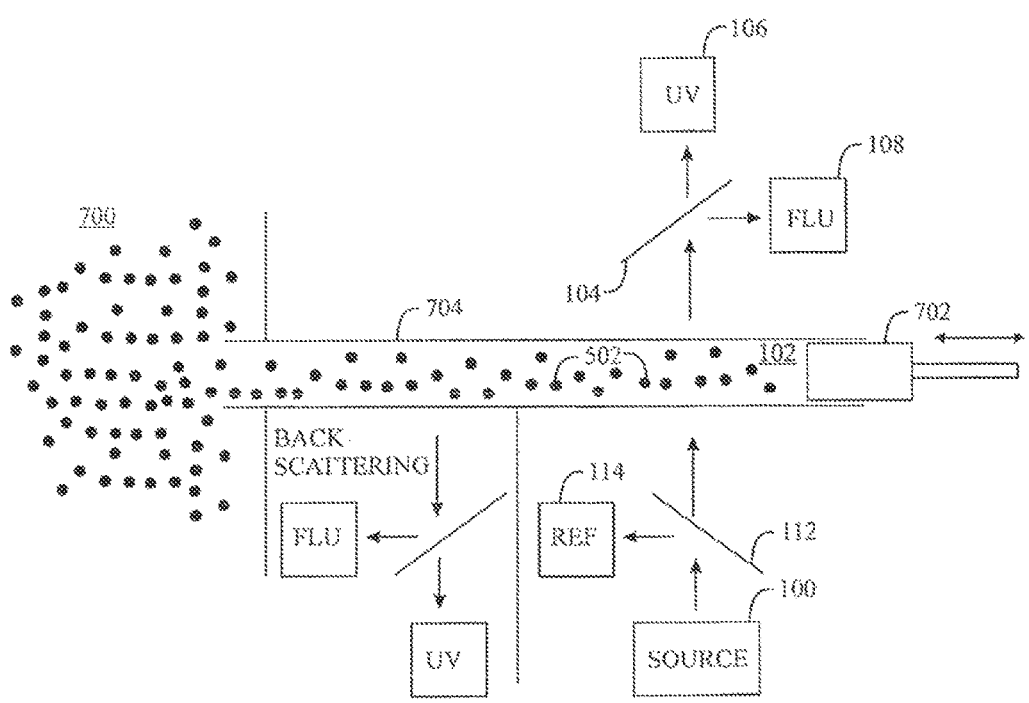
FIG. 7 shows a piston type inline sensor.

FIGS. 5, 6 and 7 describe some applications of the presented solution.

FIG. 5 presents an on-line analyzing apparatus. The by-pass line 500 may transfer a sample 102 between separate locations. The by-pass line 500 may be a pipe or a tube which is transparent in ultraviolet and visible light at a section where the measurement is made. The sample 102 may be solution or suspension.

The sample 102 may include a fluorescence marker which is used to indicate a presence or an absence of a measured object 502 (black dots) such as a particle, a microbe or a chemical. Otherwise, the measured objects may naturally generate fluorescence.

FIG. 6 presents a portable analyzing apparatus. A sample 102 such as mixture, pulp or sewage may be taken into a measurement chamber 600. A fluorescence marker may be added to the sample 102 and the marker may react with the sample if the sample 102 includes the object with which to react. If the object is non-fluorescent, the chemical reaction may make the compound fluorescent. If the object is initially fluorescent, the chemical reaction may cancel the fluorescence in the compound. After a proper mixing, the sample 102 may be fed to a measuring section 602 of the measurement chamber 600 and the sample 102 in the measuring section 602 may be measured by transmitting ultraviolet light through the measuring section 602. The signal processing unit 110 may determine a percentage of fluorescence and hence a percentage of fluorescence marker in the sample 102, for example.

If a sample 102 is taken from purified water in a water purification plant, a fluorescence marker may be added to the sample which may react with an undesirable object which may comprise various chemicals, materials, and biological contaminants in the sample. If the compound of the fluorescence marker and the object is non-fluorescent, no fluorescence or fluorescence below a predetermined threshold should be detected with the detector 108. Otherwise, the purification does not work properly. On the other hand, if the compound of the fluorescence marker and the object is fluorescent, a desired strength of fluorescence should be detected with the detector 108. Otherwise, the purification does not work properly. The strength of fluorescence may also indicate the level of purification. Hence, the signal processing unit 110 may determine whether the purification has become worse, has kept unchanged or has become better in consecutive measurements. The information may be used in planning service and/or repair of the purification plant.

FIG. 7 presents a piston type in-line sensor for the analyzing apparatus. A sample 102 may be sucked from a process 700 having solution or suspension into a cylinder 704 by a piston 702 pulled backwards from the process 700. When the sample 102 is in the cylinder 704, the measurement may be performed as described earlier by transmitting ultraviolet light through the cylinder 704. After a measurement, the sample 102 may be pushed back to the process 700 or the sample 102 may be discarded. The piston 702 cleans the tube-like cylinder 704 each time a new sample 102 is taken which is an advantage. When the piston 702 which may be non-transparent is in the optical path between the ultraviolet light source 100 and the detectors 106, 108, a dark reference may be measured with the detectors 106, 108. That is, no or below a predetermined threshold level optical radiation should be detected in that case. If too much optical radiation is detected, the apparatus should be checked due to optical leakage.

In the embodiments, the sample 102 may be solution or suspension such as pharmaceutical syrup or its pre-stage, sewage or pulp, for example. Suspension comprises a liquid medium including particles of at least one solid. The solid particles may have or may not have a special shape and the solid particles may comprise a predetermined chemical or microbe to be measured. An example of solid particles is fibres, such as animal fibres, plant fibres, cellulose fibres or synthetic fibres. The medium may be water but in a general case the medium may be some other liquid, too.

Each of the detectors 106, 108, 114, 118, 120, 308, 312, 314, 318, 320, 402 may comprise a semiconductor element such as a photodiode, a phototransistor or the like. A photodiode may be a PIN photodiode or an avalance photodiode, for example. A single detector 106, 108, 114, 118, 120, 308, 312, 314, 318, 320, 402 is an optical power meter and it does not output information on the distribution of power as a function of wavelength i.e. spectrum but only the power in the received optical band.

The measurements of optical radiation through the sample and the back scattering may be performed simultaneously. Hence, all measurements may be based on the (very) same sample at the very same moment and are hence comparable to each other.

The apparatus may be applied in process and environmental measurements.

Figure 8:
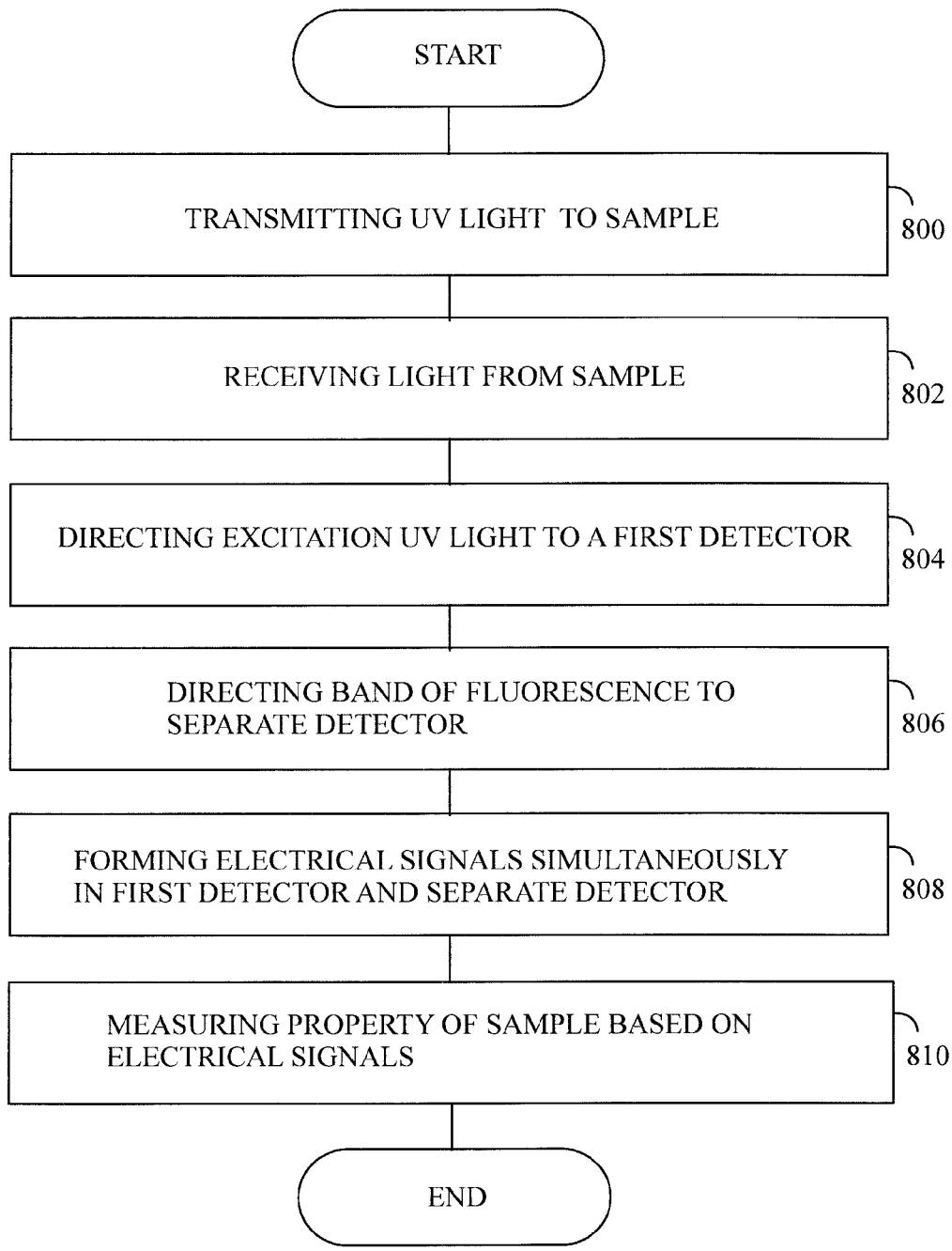
FIG. 8 shows a flow chart of the method.

FIG. 8 shows a flow chart of the method. In step 800, ultraviolet light is transmitted to a sample 102 by an ultraviolet light source 100. In step 802 a band of excitating ultraviolet light and at least one band of fluorescence associated with an interaction between the excitating ultraviolet light and the sample 102 in the optical path through the sample 102 is received from the sample 102 by a beamsplitter 104. In step 804, the band of excitating ultraviolet light passed through the sample 102 is directed towards a first detector 106 by the beamsplitter 104. In step 806, the at least one band of the fluorescence is directed towards at least one separate detector 108, 308, 408 by the beamsplitter 104. In step 808, electrical signals carrying information on powers of the bands of the ultraviolet light and the fluorescence are formed simultaneously by a first detector 106 and at least one separate detector 108, 308, 408, respectively. In step 810, at least one property of the sample 102 is measured on the basis of an optical power of the ultraviolet light and an optical power of the fluorescence in at least one separate detector 108, 308, 408 by the signal processing unit 110.

The processes or methods described in FIG. 8 may be carried out in the form of a computer process defined by a computer program. The computer program may be in source code form, object code form, or in some intermediate form, and it may be stored in a transitory or a non-transitory carrier, which may be any entity or device capable of carrying the program. Such carriers include a record medium, computer memory, read-only memory, electrical carrier signal, telecommunications signal, and software distribution package, for example. Depending on the processing power needed, the computer program may be executed in a single electronic digital processing unit or it may be distributed amongst a number of processing units.

Accordingly, the at least one processor, the memory, and the computer program code may form processing means for carrying out embodiments.

Potential implementations of the embodiments of the signal processing unit 110 may be a combination of processor(s) or portions of processors/software including digital signal processor(s), software, and memory(ies) that work together to cause an apparatus to perform various functions and/or a microprocessor(s) or a portion of a microprocessor(s), that require software or firmware for operation, even if the software or firmware is not physically present. In an embodiment, a computing unit may comprise separate processor components such that the processes or methods described in FIG. 8 acts are performed in the processing system comprising a plurality of processing units and a load-balancing logic for distributing processing load among the multiple processing units. In an embodiment, at least one processing unit may receive a command to start the process from an interface, for example, and another processing unit or units may perform the steps of FIG. 8.

It will be obvious to a person skilled in the art that, as technology advances, the inventive concept can be implemented in various ways. The invention and its embodiments are not limited to the examples described above but may vary within the scope of the claims.

The invention claimed is:

1. An optical apparatus, characterized in that the apparatus comprises an ultraviolet light source configured to transmit the ultraviolet light to a sample, one or more wavelength dependent beam splitters, at least one backscattering beam splitter, at least two back scattering detectors, and at least two separate detectors, wherein:
   each beam splitter is configured to receive, from the sample, a band of excitating ultraviolet light and at least one band of fluorescence associated with an interaction between the excitating ultraviolet light and the sample in the optical path through the sample, to direct the band of excitating ultraviolet light passed through the sample towards a first detector, and to direct the at least one band of the fluorescence towards at least one separate detector;
   the first detector and the at least one separate detector are simultaneously configured to form electrical signals carrying information on powers of the bands of the ultraviolet light and the fluorescence, respectively;

the at least one backscattering beam splitter is configured to receive ultraviolet light and fluorescence scattered backwards from the sample from a direction different from parallel to the transmitted ultraviolet light, and direct them to different back scattering detectors;

the at least two back scattering detectors are configured to separately detect ultraviolet light and fluorescence scattered backwards from the sample; and a signal processing unit is configured to measure the at least one property of the sample on the basis of a signal from the first detector and each signal from the at least one separate detector, and to calibrate the measurement of the at least one property on the basis of the back scattering for compensating additional scattering in the optical path or in the sample.

2. The apparatus of claim 1, characterized in that the signal processing unit is configured to determine a percentage of a fluorescent marker in the sample.

3. The apparatus of claim 1 or 2, characterized in that apparatus comprises partially transparent reflector and a reference detector, the transparent reflector being placeable between the ultraviolet light source and the sample for reflecting a part of the ultraviolet light transmitted by the ultraviolet light source to the reference detector for measuring the transmission power of the ultraviolet light source and for scaling the powers of the ultraviolet light and the fluorescence in the signal processing unit.

4. The apparatus of claim 1, characterized in that the ultraviolet light source is configured to transmit ultraviolet light pulses periodically.

5. The apparatus of claim 4, characterized in that the signal processing unit is configured to receive information on each light pulse transmitted by the ultraviolet light source for scaling the powers of detected ultraviolet light pulses and the corresponding pulses of fluorescence in the signal processing unit.

6. The apparatus of claim 1, characterized in that the apparatus is used as an online analyzer wherein the ultraviolet light source is configured to transmit the ultraviolet light through a by-pass line containing the sample; and each beam splitter is configured to receive, from the sample in the by-pass line, a band of excitating ultraviolet light and at least one band of fluorescence associated with an interaction between the excitating ultraviolet light and the sample.

7. The apparatus of claim 1, characterized in that the apparatus is used as a portable kit wherein the apparatus comprises a measurement chamber and a measuring section coupled to the measurement chamber; the ultraviolet light source is configured to transmit the ultraviolet light through the measuring section containing the sample; and each beam splitter is configured to receive, from the sample in the measuring section, a band of excitating ultraviolet light and at least one band of fluorescence associated with an interaction between the excitating ultraviolet light and the sample.

8. The apparatus of claim 1, characterized in that the apparatus comprises a cylinder and a piston wherein the cylinder is configured to be coupled to a process;

the piston is configured to suck the sample from the process to the cylinder when moved backwards in the cylinder;

the ultraviolet light source is configured to transmit the ultraviolet light through the cylinder containing the sample; and each beam splitter is configured to receive, from the sample in the cylinder, a band of excitating ultraviolet light and at least one band of fluorescence associated with an interaction between the excitating ultraviolet light and the sample.

9. An optical method, characterized by:

transmitting by an ultraviolet light source ultraviolet light to a sample;

detecting, by at least two back scattering detectors, ultraviolet optical radiation and fluorescence scattered backwards from the sample from a direction different from parallel to the transmitted ultraviolet light;

receiving, from the sample, a band of excitating ultraviolet light and at least one band of fluorescence associated with an interaction between the excitating ultraviolet light and the sample in the optical path through the sample, directing the band of excitating ultraviolet light passed through the sample towards a first detector, and directing the at least one band of the fluorescence towards at least one separate detector by a beamsplitter;

forming simultaneously, by the first detector and at least one separate detector, electrical signals carrying information on powers of the of the bands of the ultraviolet light and the fluorescence, respectively;

measuring, by a signal processing unit, at least one property of the sample on the basis of an optical power of the ultraviolet light and an optical power of the fluorescence in at least one separate detector; and calibrating, by the signal processing unit, the measurement of the at least one property on the basis of the back scattering for compensating additional scattering in the optical path or in the sample.

10. The method of claim 9, characterized by determining, in the processing unit, a percentage of a fluorescent marker in the sample.

11. The method of claim 9 or 10, characterized by reflecting by a partially transparent reflector a part of the ultraviolet light transmitted by the ultraviolet light source to the reference detector for measuring the transmission power of the ultraviolet light source and scaling the powers of the ultraviolet light and the fluorescence in the signal processing unit.

12. The method of claim 11, characterized by transmitting, by the ultraviolet light source, ultraviolet light pulses periodically.

13. The method of claim 12, characterized by measuring, in the signal processing unit, each light pulse transmitted by the ultraviolet light source for scaling the powers of detected ultraviolet light pulses and the corresponding pulses of fluorescence in the signal processing unit.

14. The method of claim 9, characterized by transmitting the ultraviolet light of the ultraviolet source though a by-pass line of an online analyzer, the by-pass line containing the sample; and receiving a band of excitating ultraviolet light and at least one band of fluorescence associated with an interaction between the excitating ultraviolet light and the sample from the sample in the by-pass line by each beam splitter.

15. The method of claim 9, characterized by transmitting the ultraviolet light of the ultraviolet source though a measuring section coupled to a measurement chamber of a portable kit, the measuring section containing the sample; and receiving a band of excitating ultraviolet light and at least one band of fluorescence associated with an interaction between the excitating ultraviolet light and the sample from the sample in the measuring section by each beam splitter.

16. The method of claim 9, characterized by sucking, by a piston, the sample from a process to a cylinder by moving the piston backwards in the cylinder;

transmitting the ultraviolet light of the ultraviolet light source though the cylinder which contains the sample; and receiving a band of excitating ultraviolet light and at least one band of fluorescence associated with an interaction between the excitating ultraviolet light and the sample from the sample in the cylinder by each beam splitter.

17. A computer program product embodied on a distribution medium readable by a computer and comprising program instructions which, when loaded into an apparatus, execute a computer process comprising the method steps of claim 9.

18. An apparatus comprising:

at least one processor; and at least one memory including a computer program code, wherein the at least one memory and the computer program code are configured, with the at least one processor, to cause the apparatus to:

detect, by at least two back scattering detectors ultraviolet optical radiation and fluorescence scattered backwards from the sample from a direction different from parallel to the transmitted ultraviolet light;

transmit, by an ultraviolet light source, ultraviolet light to a sample;

form simultaneously, by a first detector and at least one separate detector, electrical signals carrying information on powers of the of the bands of the ultraviolet light and the fluorescence, respectively, on the basis of splitting, by a beamsplitter, of a band of excitating ultraviolet light and at least one band of fluorescence associated with an interaction between the excitating ultraviolet light and the sample in the optical path through the sample towards the first detector, and the at least one separate detector;

measure, in a signal processing unit, at least one property of the sample on the basis of an optical power of the ultraviolet light and an optical power of the fluorescence in at least one separate detector; and calibrate, by the signal processing unit, the measurement of the at least one property on the basis of the back scattering for compensating additional scattering in the optical path or in the sample.

* * * * *